United States Patent [19]

Smith

[11] 3,932,190
[45] Jan. 13, 1976

[54] PLASTER OF PARIS BANDAGES BONDED WITH MINIMAL PROPORTIONS OF HYDROLYZED POLYVINYL ESTERS

[76] Inventor: David F. Smith, 315 Washington Blvd., Sea Girt, N.J. 08750

[22] Filed: July 30, 1973

[21] Appl. No.: 383,691

[52] U.S. Cl. .................................. 106/111; 128/91
[51] Int. Cl.² ........................................ C04B 11/14
[58] Field of Search ........................... 106/111–115; 128/91

[56] References Cited
UNITED STATES PATENTS
3,649,319   3/1972   Smith .................................. 106/114

*Primary Examiner*—Patrick P. Garvin
*Assistant Examiner*—John P. Sheehan

[57] ABSTRACT

Minimal proportions of hydrolyzed polyvinyl esters are effective bonding agents in plaster of Paris bandages.

13 Claims, No Drawings

PLASTER OF PARIS BANDAGES BONDED WITH MINIMAL PROPORTIONS OF HYDROLYZED POLYVINYL ESTERS

In my U.S. Pat. No. 3,649,319, issued Mar. 14, 1972, I have disclosed plaster of Paris bandages bonded with 1–15% of hydrolyzed polyvinyl esters. I have now discovered that excellent bonding can be obtained with as little as 0.2% of the weight of the plaster.

There are relatively few bonding agents that can be used since most of them show one or more of the following disadvantages: interfere with the set, reduce cast strength, slow wetting of the bandage, impart a harsh feel to the wet bandage, may have toxic, irritating or allergenic properties, do not bond both dry and wet bandage, are required in too large amounts, increase moisture-sensitivity of the bandage, are too costly or encourage bacterial, mold or enzyme action. All these difficulties are substantially avoided in my use of hydrolyzed polyvinyl esters.

Use of minimal proportions of bonding agent is highly desirable not only from the standpoints of cost of the material and its preparation for my use but also it is usually found that most extraneous materials reduce cast strength.

I have noted in my above-cited patent that use of hydrolyzed polyvinyl esters may, under certain conditions, result in the presence in the wet bandage of "cords" that detract from a smooth feel that is desired. I have eliminated these curds by vigorous stirring of the plaster slurry used to coat the backing but it is convenient if a "softening agent" is used in the slurry, comprising up to 1% of the weight of plaster of cooked starch in aqueous solution, dextrin in aqueous solution, cooked ethylated starch in aqueous solution (with up to 0.06% substitution of ethyl groups by reaction with ethylene oxide), polyvinyl pyrrolidone, dextran, methyl cellulose, hydroxyethyl ethyl cellulose or hydroxypropyl methyl cellulose. I have also now discovered that the curds can be eliminated by using a mixture of hydrolyzed polyvinyl esters of different degree of hydrolysis and/or different degree of polymerization. As a matter of fact these softening agents or mixtures offer a means of controlling both wet and dry plaster-loss as well as the texture, consistency and smoothing-out the plaster in the wet bandage.

The hydrolyzed polyvinyl esters I find useful, vary in degree of hydrolysis and polymerization from about 80 to 100% (99.8%) and 5 to 80 centipoises viscosity as measured in 4 weight % aqueous solution at 20°C. measured by the Hoeppler falling-ball method, respectively. The higher the hydrolysis and the higher the polymerization (viscosity) the better the bonding as the bandage is wet in water and the excess water squeezed out, preparatory to making a cast. The softening agents and the nature of the ester are also used to control dusting of the dry bandage. The curds are more prevalent when using an ester of high hydrolysis and high viscosity, but even then they can be avoided by adequate stirring of the slurry or, more conveniently, by use of the softening agents and ester mixtures cited. I can reduce plaster-loss from the wet bandage to less than 1% of the weight of the dry bandage, as determined by the method of Federal Specification GG-B-101d and in any case I have no difficulty in meeting the specified upper limit of 10 %.

The following Examples illustrate specific embodiments of my invention variations of which within the scope of the appended claims, will be evident to those skilled in the art. (All test results are obtained by the said Federal Specification methods.)

EXAMPLE 1

54 grams of hydrolyzed polyvinyl acetate (pva) with degree of hydrolysis of 99–100% and viscosity of 60–70 cps. and 18 grams pva of 99–100% hydrolysis and viscosity 5.1–6.2 cps. were dissolved in 2000 grams water by heating in a steam bath at 180°–210°F. for one-half hr. The cooled solution was stirred into 2.6 gallons of 29.4 wt.% $NH_3$ (commercial aqua ammonia, ca. 30% $NH_3$). Then there was stirred in 10 grams casein (commercial "Argentina acid" casein) and 373 grams powdered $K_2SO_4$. Finally 18,140 grams of steam-calcined plaster of Paris (hereinafter designated pop, of 99% through 200 mesh U.S. standard screen) was thoroughly stirred in for 20 minutes. The slurry was then coated on 32 × 28 mesh/inch surgical gauze and dried at about 235°F. for about 2 minutes to yield a dry product weighing 220–238 grams per 5 sq. ft. (a 4 inch × 5 yd. bandage). The product set in 4 min. and had a cast strength of 528 lbs. at one-half hour for a 222 gram dry bandage. The wet plaster-loss was 1.35% and the wet bandage had a soft, smooth feel.

EXAMPLE 2

90 grams of pva of 99–100% hydrolysis and 60–70 cps. viscosity was dissolved as in Example 1. This was thoroughly stirred into 2.6 gal. aqua ammonia and 10 grams casein and 373 grams powdered $K_2SO_4$ added. Then 18,140 g. pop was thoroughly stirred in as before and coated and dried as before. The final bandage had a set of 4:30 min., a cast strength of 542 lbs. at one-half hr. using a 239 g. bandage and a wet plaster-loss of less than 1%. However the wet bandage was not as creamy in feel as that of Example 1 and was less readily smoothed out in the cast.

EXAMPLE 3

This experiment was made as in Experiment 1, except that, for the 18 grams of the second pva, was substituted 18 g. of 99–100% hydrolyzed pva of viscosity 25–35 cps. The product set in 4:12 min., had a one-half hr. cast strength of 552 lbs. for a 235 g. dry bandage and a wet plaster-loss of 2.4%. The wet bandage was smooth.

EXAMPLE 4

This experiment was made as in Ex. 1 but used 45 g. of pva of 99–199% hydrolysis and 60–70 cps. viscosity with 27 g. pva of 99–100% hydrolysis and 25–35 cps. viscosity. The set was 4 min., the one-half hr. cast strength was 531 lbs. with a dry bandage weight of 231 g. and the wet plaster-loss was 3.8%. The wet bandage was smooth.

EXAMPLE 5

This experiment was run as in Ex. 1 but with no casein and with 54 g. pva of 99–100% hydrolysis and 60–70 cps. viscosity and 18 g. pva of 99–100% hydrolysis and 5–6 cps viscosity. The set was 3:30 min., the one-half hr. cast strength 594 lbs. with a 236 g. dry bandage and the wet plaster-loss was 0.7%. The wet bandage was smooth.

EXAMPLE 6

This experiment was run as in Ex. 1 but used 54 g. pva of 99–100% hydrolysis and 60–70 cps. viscosity plus 18 g. corn starch dextrin that had been dissolved in hot water. The set was 4:56 min., the one-half hr. cast strength 508 lbs. with a 220 g. dry bandage and the wet plaster-loss was 4.9%. The thoroughly dry cast showed exceptionally high cast strength and the wet bandage was smooth and creamy.

EXAMPLE 7

This experiment was again run as in Ex. 1 but with 54 g. pva of 99–100% hydrolysis and 60–70 cps. viscosity, 9 g. pva of 99–100% hydrolysis and 25–35 cps. viscosity and 9 g. of pva of 98–99% hydrolysis and 25–31 cps. viscosity. No casein was used. The set was 3:15 min., the one-half hr. cast strength 560 lbs. with a dry bandage weighing 231 g. and the wet plaster-loss was 0.5%.

A much larger-scale run was made using pva of 99–100% hydrolysis and 60–70 cps. viscosity in amount equal to 0.3% of the weight of plaster plus pva of 98–99% hydrolysis and 6–8 cps. viscosity in amount of 0.1% of the weight of plaster, and casein in amount of 0.049% of the weight of plaster. The product had a set of 3:15 min., a one-half hr. cast strength up to 624 lbs. with a dry bandage weighing 238 g. and a wet plaster-loss of 2.3%. This run provided more efficient stirring of the slurry and a long enough run to permit adjustment of the variables to somewhere near to the optimum. The wet bandage was extremely smooth and gave a high-strength cast even 6 minutes after the bandage was wet to make the cast.

It is thus evident with properly controlled operation and highly efficient mixing of the slurry, bonding of the wet bandage can meet government specifications with as little as a total of pva equal to 0.1 to 0.2% of the weight of plaster of Paris.

In using mixtures of the esters, it is usual to combine an ester of high hydrolysis and viscosity with one or more having lower hydrolysis and/or viscosity. For example, the % dissolved in water at 20°C. in stirring 4 parts ester in 96 parts water for 30 min. is 6% for 98–99% hydrolyzed ester of 50–62 cps.; 31% for 98–99% hydrolysed ester of 5.2–6 cps. and 83% for 87–89% hydrolyzed ester of 39–47 cps. The ester with high hydrolysis and high viscosity is the wet bonding agent of most effectiveness while the more soluble material plasticizes it and controls dusting of the dry bandage.

The dextrin used is dissolved by heating in water at about 180°F. for a few minutes. The starch or ethylated starch is cooked in boiling water for 1–2 hrs. at a concentration of not over about 12 weight %. The dextran used is water-soluble, is made by action of bacteria on sucrose and has a molecular-weight of from 75,000–40,000,000. The other softening agents are readily soluble in cold water. I use the softening agent in amount from 0–100% of the weight of the pva of the higher hydrolysis and higher viscosity. The plaster set-accelerator, $K_2SO_4$, is used in amount from 0.5–2.5% of the weight of plaster. My disclosure will be described in terms of the acetate ester but the useful propionate and butyrate are characterized by about the same % hydrolysis and viscosity. When using casein or boric acid as set-inhibitors in the aqueous slurry they are dissolved in aqueous ammonia from about 1–30% $NH_3$ by weight and in amount from about 0.025 to 1% of the weight of plaster, the casein being about twice as effective as the boric acid for the same concentration. With casein or boric acid in very low concentration, the aqueous ammonia is used at the higher concentration of from about 8–30% $NH_3$ based on weight of water plus $NH_3$ since it has a synergistic effect in delaying the set of the aqueous slurry. In this connection I have found that there is also this synergistic action between the polyvinyl esters and $NH_3$. For example in an aqueous slurry containing 24 wt.% $NH_3$ and 0.67 wt.% pva, the set of plaster is delayed for over 60 hrs. while, without the $NH_3$, the set is a few minutes and without the pva, the set is about 1 hr. Since without casein or boric acid, there is no residual ammonium salt of these inhibitors left in the dried bandage, one obtains a very fast-setting product. This synergism is present with pva concentrations of more than about 0.4% of the weight of the slurry liquid and from 8–30 wt.% $NH_3$ in the liquid.

It is not necessary that the set accelerator be dissolved in the slurry liquid, although it usually will be, but both it and the pop should be fine enough to pass a 100 mesh/inch U.S. standard mesh screen in order not to impart a gritty feel to the wet bandage.

Having thus described my invention, what I claim is:

1. A dry, bonded plaster of Paris bandage comprising a flexible, inert, porous, water absorbent backing material coated to the extent of from 40 to 50 grams per square foot with an essentially uniform mixture comprising a major proportion of settable, powdered plaster of Paris:
   1. from 0.5 to 2.5 per cent of the weight of plaster of finely divided potassium sulfate; and
   2. a mixture of a least two hydrolyzed polyvinyl esters selected from the group consisting of acetate, propionate and butyrate in a total amount of from 0.1 to 1 per cent of the weight of plaster and having a degree of hydrolysis of from 80 to 100 per cent and a viscosity of between 5 to 80 centipoise in a 4 per cent aqueous solution at 20°C as determined by the Hoeppler falling-ball method, where at least one of the esters is present in an amount of up to 100 per cent of the weight of the first and having a degree of hydrolysis and a viscosity respectively in the same range but substantially different in at least one of the properties of degree of hydrolysis and viscosity.

2. The bandage of claim 1 wherein the second ester has a degree of hydrolysis of 98 to 99 per cent.

3. The bandage of claim 1 wherein said esters are acetates, where the first ester is present in the amount of 0.1 per cent with a viscosity of from 60 to 70 centipoise and a degree of hydrolysis of from 99 to 100 per cent and the second ester is present in the amount of 0.1 per cent and a degree of hydrolysis of from 99 to 100 percent and a viscosity of from 25 to 35 centipoise.

4. The bandage of claim 1 wherein said esters are two acetates, where the first ester is present in the amount of 0.1 per cent with a viscosity of from 60 to 70 centipoise and a degree of hydrolysis of from 99 to 100 per cent and the second ester is present in the amount of 0.1 per cent with a degree of hydrolysis of from 99 to 100 per cent and a viscosity of 5 to 7 centipoise.

5. The bandage of claim 1 which in addition contains a material in the amount of from 0 to 1 per cent of the weight of the plaster which is selected from the group consisting of casein and boric acid.

6. The bandage of claim 1 wherein the esters are two polyvinyl acetate esters, the first ester being present in the amount of from 0.1 to 0.3 per cent of the weight of the plaster and having a degree of hydrolysis of from 99 to 100 per cent with a viscosity of 60 to 70 Centipoise, the second ester being present in the amount of 0.1 to 0.3 per cent of the weight of the plaster and having a degree of hydrolysis of from 99 to 100 per cent with a viscosity of 5 to 7 centipose.

7. The bandage of claim 1 which in addition contains:
1. a softening agent in the amount of from 0 to 1 per cent of the amount of the plaster and selected from the group consisting of dextrin, dextran, cooked starch, cooked ethylated starch with up to 0.06 per cent substitution of ethyl groups, polyvinyl pyrrolidone, methyl cellulose, hydroxyethyl ethyl cellulose and hydroxypropyl methyl cellulose; and
2. a material in the amount of 0 to 1 per cent of the weight of the plaster, and selected from the group consisting of casein and boric acid.

8. The bandage of claim 7 wherein the esters are two polyvinyl acetate esters, the first ester being present in the amount of from 0.1 to 0.3 per cent of the weight of the plaster and having a degree of hydrolysis of from 99 to 100 per cent with a viscosity of 60 to 70 centipoise, the second ester being present in the amount of from 0.1 to 0.3 per cent of the weight of the plaster and having a degree of hydrolysis of from 99 to 100 per cent with a viscosity of 5 to 7 centipoise.

9. The bandage of claim 7 wherein the esters are two polyvinyl acetate esters, the first ester being present in the amount of from 0.1 to 0.3 per cent of the weight of the plaster and having a degree of hydrolysis of from 99 to 100 per cent and a viscosity of 60 to 70 centipoise, the second ester being present in the amount of 0.1 to 0.3 per cent of the weight of the plaster and having a degree of hydrolysis of from 98 to 99 per cent and a viscosity of 5 to 7 centipoise.

10. The bandage of claim 7 wherein the esters are two polyvinyl acetate esters, the first ester being present in the amount of from 0.1 to 0.3 per cent of the weight of the plaster and having a degree of hydrolysis of from 99 to 100 per cent and a viscosity of 60 to 70 centipoise, the second ester being present in the amount of from 0.1 to 0.3 per cent of the weight of the plaster and having a degree of hydrolysis of from 99 to 100 per cent with a viscosity of from 25 to 35 centipoise.

11. A dry, bonded plaster of Paris bandage comprising a flexible, inert, porous, water absorbent backing material coated to the extent of from 40 to 50 grams per square foot with an essentially uniform mixture comprising a major proportion of wettable, powdered plaster of Paris:
1. from 0.5 to 2.5 per cent of the weight of the plaster of finely divided potassium sulfate; and
2. from 0.3 to 0.5 per cent of a 99 to 100 per cent hydrolyzed polyvinyl acetate with a viscosity of 60 to 70 centipoise.

12. The bandage of claim 11 which in addition contains:
1. a softening agent in the amount of from 0 to 1 per cent of the amount of plaster and selected from the group consisting of dextrin, dextran, cooked starch, cooked ethylated starch with up to 0.06 per cent substitution of ethyl groups, polyvinyl pyrrolidone, methyl cellulose, hydroxy ethyl ethyl cellulose and hydropropyl methyl cellulose, and
2. a material in the amount of from 0 to 1 per cent of the weight of the plaster and selected from the group consisting of casein and boric acid.

13. A settable plaster of Paris mix comprising a major proportion of powdered plaster of Paris and water; from 0.5 to 2.5 per cent of the weight of the plaster of powdered potassium sulfate; from about 8 to 30 per cent ammonia based on the weight of the water and ammonia; and at least 0.4 per cent of the weight of the amonia and water of hydrolyzed polyvinyl acetate having a degree of hydrolysis of from 80 to 100 percent and a viscosity of 5 to 80 centipoise at 20°C in a 4 weight per cent aqueous solution as determined by the Hoeppler falling-ball method, said ammonia and polyvinyl acetate being dissolved.

* * * * *